United States Patent [19]

Dingwall et al.

[11] 4,363,923
[45] Dec. 14, 1982

[54] 4-HALGENO-OXETAN-2-ONES AND PROCESS FOR THEIR PRODUCTION

[75] Inventors: John G. Dingwall, Sale; Brian Tuck, Stockport, both of England

[73] Assignee: Ciba-Geigy Corporation, Ardsley, N.Y.

[21] Appl. No.: 248,373

[22] Filed: Mar. 27, 1981

[30] Foreign Application Priority Data

Mar. 27, 1980 [GB] United Kingdom ................. 8010384

[51] Int. Cl.$^3$ ...................... C07D 305/12; B01J 19/12
[52] U.S. Cl. ................................. 549/329; 204/158 R
[58] Field of Search ..................... 260/343.9; 549/329; 204/158 R

[56] References Cited

U.S. PATENT DOCUMENTS 2,585,537  2/1952  Coffman .
2,675,392  4/1954  Theobald .

FOREIGN PATENT DOCUMENTS 1136323  9/1962  Fed. Rep. of Germany .
1025469  4/1966  United Kingdom ............. 260/343.9

OTHER PUBLICATIONS

Kleemann et al., Chem. Ber., vol. 112, pp. 1140–1146 (1979).
Houben–Weyl, Methoden der Organischen Chemie, (1960), vol. 5/4, pp. 469–474.
Houben–Weyl, Methoden der Organischen Chemie, (1962), vol. 5/3, pp. 971–976.

*Primary Examiner*—Norma S. Milestone
*Attorney, Agent, or Firm*—Michael W. Glynn

[57] ABSTRACT

Novel compounds having the formula I

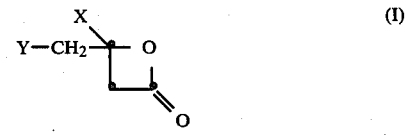

are described wherein X is a chlorine, bromine or iodine atom and Y is a residue having the formula $R^1R^2R^3C-$ wherein $R^1$ and $R^2$ are the same or different and each is a fluorine, chlorine or bromine atom and $R^3$ is a hydrogen, fluorine, chlorine or bromine atom, a group $-CR^4R^5R^6$, a cyano group, a group $-COR^7$ or $-PO(R^8)_2$ wherein $R^4$, $R^5$, $R^6$, independently, are F, Cl or Br, $R^7$ nd $R^8$ are the same or different and each is a chlorine atom or a group $-OR^9$ wherein $R^9$ is a $C_1$–$C_4$ straight chain or branched alkyl group with the proviso that when X is a chlorine atom, none of $R^1$, $R^2$, $R^3$, $R^4$, $R^5$ and $R^6$, can be a bromine atom.

They can be obtained by reacting diketene with a compound XY in the presence of an agent capable of forming free radicals. Compounds (I) have biocidal activity against various organisms, e.g. bacteria, fungi and algae.

9 Claims, No Drawings

4-HALGENO-OXETAN-2-ONES AND PROCESS FOR THEIR PRODUCTION

The present invention relates to new 4-halogenooxetan-2-ones and a process for their production.

According to the present invention, there are provided compounds having the formula I

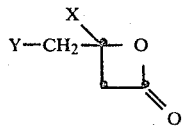

wherein X is a chlorine, bromine or iodine atom and Y is a residue having the formula $R^1R^2R^3C-$, wherein $R^1$ and $R^2$ are the same or different and each is a fluorine, chlorine or bromine atom and $R^3$ is a hydrogen, fluorine, chlorine or bromine atom, a group $-CR^4R^5R^6$, a cyano group, a group $-COR^7$ or $-PO(R^8)_2$ wherein $R^4$, $R^5$, $R^6$, independently, are F, Cl or Br, $R^7$ and $R^8$ are the same or different and each is a chlorine atom or a group $-OR^9$ wherein $R^9$ is a $C_1-C_4$ straight chain or branched alkyl group with the proviso that when X is a chlorine atom, none of $R^1$, $R^2$, $R^3$, $R^4$, $R^5$ and $R^6$ can be a bromine atom.

When $R^9$ is a $C_1-C_4$ alkyl group, it may be a methyl, ethyl, n-propyl, isopropyl, n-butyl, sec.butyl or t-butyl group. X preferably represents a chlorine or bromine atom. $R^1$, $R^2$ and $R^3$ preferably are each a fluorine, chlorine or bromine atom. Specific Examples of compounds of formula I include:

4-Chloro-4-(2,2,2-trichloroethyl)oxetan-2-one, 4-bromo-4-(2-chloro-2,2-difluoroethyl)oxetan-2-one, 4-bromo-4-(2-bromo-2,2-difluoroethyl)-oxetane-2-one, 4-bromo-4-(2,2,2-trichloroethyl)oxetan-2-one, 4-bromo-4-(2-bromo-2,2-dichloroethyl)oxetan-2-one, 4-bromo-4-(2,2,2-tribromoethyl)oxetan-2-one, 4-chloro-4-(2-chlorocarbonyl-2,2-dichloroethyl)-oxetan-2-one, 4-chloro-4-(2,2-dichloro-2-methoxycarbonylethyl)oxetan-2-one, 4-chloro-4-(2,2-dichloro-2-ethoxycarbonylethyl)oxetan-2-one, 4-chloro-4-(2,2-dichloro-2-n-butoxycarbonylethyl)oxetan-2-one, 4-chloro-4-(2,2-dichloro-2-dichlorophosphonylethyl)oxetan-2-one, 4-chloro-4-(2,2-dichloro-2-diethylphosphonoethyl)oxetan-2-one, 4-chloro-4-(2,2-dichloro-2-cyanoethyl)oxetan-2-one, 4-bromo-4-(2,2-dibromo-2-methoxycarbonylethyl)oxetan-2-one, 4-bromo-4-(2,2-dibromo-2-cyanoethyl)oxetan-2-one, 4-chloro-4-(2,2,3,3,3-pentachloropropyl)-oxetan-2-one, 4-bromo-4-(2-bromo-2,3,3,3-tetrachloropropyl)oxetan-2-one, 4-bromo-4-(2-bromo-2-chloro-3,3,3-trifluoropropyl)oxetan-2-one, and 4-iodo-4-(2,2,2-trifluoroethyl)oxetan-2-one.

Preferred compounds of formula I include: 4-Chloro-4-(2,2,2-trichloroethyl)oxetan-2-one, 4-bromo-4-(2,2,2-trichloroethyl)oxetan-2-one, 4-bromo-4-(2,2,2-tribromoethyl)oxetan-2-one, 4-chloro-4-(2,2-dichloro-2-ethoxycarbonyl-ethyl)oxetan-2-one, and 4-bromo-4-(2-chloro-2-bromo-3,3,3-trifluoropropyl)oxetan-2-one.

The present invention also provides a process for the production of compounds of formula I comprising reacting diketene with a compound XY in the presence of an agent capable of forming free radicals.

Examples of compounds XY are tetrahalomethanes such as carbontetrachloride, carbontetrabromide or bromotrichloromethane; trihalomethyl compounds such as ethyltrichloroacetate, trichloromethylphosphonyldichloride, trichloroacetonitrile, 1-chloro-1,1-dibromotrifluoroethane or hexachloroethane.

Agents forming free radicals include for example:
(i) Ionising radiation;
(ii) Ultraviolet radiation;
(iii) Organic peroxides e.g. t-butylperacetate, t-butylperbenzoate, acetylperoxide, benzoylperoxide, di-isopropylperdicarbonate, bis-(t-butylcyclohexyl)-perdicarbonate, di-t-butylperoxide, and t-butylhydroperoxide;
(iv) Inorganic peroxy compounds e.g. hydrogen peroxide and ammonium persulphate;
(v) Organic azo compounds e.g. azobisisobutyronitrile, and azobisisopropane;
(vi) Combination of (iii) or (v) with ultraviolet radiation;
(vii) Combination of (iii) or (iv), with a metal ion catalyst, e.g. Cu, Ti, V, Fe to give a radical producing redox-system e.g.

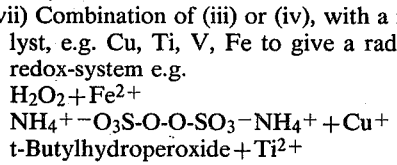

Preferred agents forming free radicals are organic peroxides, organic azo compounds, and combinations of organic peroxides or organic azo compounds with ultraviolet radiation.

The radical forming substances [(iii), (iv), (v)] may be used advantageously in catalytic amounts of 0.1–10 mol%, preferably 1–5 mol%, based on diketene. The preferred molar ratio of compound XY to diketene is from 1:1 to 20:1. In the above process, the reactant XY may act as the solvent but, if desired, the reaction may optionally be carried out in the presence of a solvent inert under the reaction conditions e.g. petroleum ether in low temperature reactions; benzene, toluene or carbon tetrachloride in moderate temperature reactions; or chlorobenzene in high temperature reactions. The reaction may be effected under conditions well-known per se e.g. in the temperature range $-20°$ C. to $150°$ C., according to the radical producing method employed, preferably between $0°$ C. to $100°$ C.; and, if the compound XY is a gas, optionally in an inert gas atmosphere and optionally under pressure. The reactions can be carried out batchwise, or, preferably, in a continuous manner, for example in a cascade reactor.

Compounds of formula I show broad spectrum biocidal activity in the range of 1000 $\mu g/ml$ and lower against a range of organisms. In particular the compounds of formula I control the growth of bacteria, fungi and algae, at low concentration. The compounds of formula I are also useful as intermediates for a wide variety of chemicals.

They are particularly effective in controlling the growth of bacteria, fungi and algae in still or circulating water systems, for example in industrial cooling towers, swimming pools etc., in other aqueous-based or oil-based systems e.g. cutting fluids and secondary oil recovery processes; in industrial processing waters e.g. processing waters in wood, pulp, paper, textiles and leather processing; and in surface disinfection e.g. in hospitals, dairies etc.

The compounds of formula I can be applied as biocides in pure form or as concentrated or dilute solutions or emulsions, which may be optionally stabilised with alkali- or alkaline earth metal carbonates. It is also possible to apply them in admixture with solid carriers. The compounds can also be applied as suspensions in liquid compositions, in which case wetting agents or emulsifiers may be used to assist the distribution of the active ingredient to form homogeneous dispersions. If desired, the compounds may be used together with other biocides.

One field of application is the treatment of cooling water. For protection against the growth of microorganisms, the active compounds can advantageously be added direct to the cooling water.

When using the compounds for treating water, it is possible to add simultaneously other additives, for example, corrosion inhibitors, antiincrustants, water softeners, complexing agents and low foaming surfactants or penetrants, for example, polymeric phosphites, phophates, amides of phosphoric acids, polymeric carboxylic acids or anhydrides, for example polyacrylic acids or polymaleic acids, or salts thereof and other additives.

Organisms whose growth is controlled include for example:

| Class/type | Examples | Problems caused |
|---|---|---|
| Algae | | |
| Green | Chlorella vulgaris | General matting |
| | Chlorella pyrenoidosa | and fouling |
| | Scenedesmus spec. | usually by |
| | Ulothrix subtilissima | blocking of pipes |
| Blue-green | Oscillatoria geminata | pumps, filters, etc. |
| | Nostoc spec. | |
| | Phormidium foveolarum | |
| | Anacystis nidulans | |
| Brown | Tribonema aequale | |
| Bacteria | | |
| Gram positive | Bacillus cereus var. mycoides | Bacterial slimes |
| | Bacillus subtilis | produced which |
| | Streptomyces griseus | cause reduced |
| | Streptomyces aureofasciculus | plant efficiency |
| | Staphylococcus aureus | and increased |
| Gram negative | Pseudomonas aeruginosa | corrosion. |
| | Aerobacter aerogenes | plant efficiency |
| | Serratia marcescens | |
| | Alcaligenes denitrificans | |
| | Escherichia coli | |
| | Proteus vulgaris | |
| Anaerobic | Desulphovibrio desulphuricans | $H_2S$ produced |
| Sulphate | | with resultant |
| reducing | | severe corrosion. |
| Fungi | Aspergillus niger | Surface rot, |
| | Aspergillus phoenicus | discoloration, |
| | Penicillium funiculosum | slime production |
| | Alternaria alternata | and internal |
| | Cladosporium cladosporioides | wood decay. |
| | Candida albicans | |
| | Endomyces geotrichum | |
| | Aureobasidium pullulans | |

The following Examples, in which parts and percentages are by weight, further illustrate the present invention.

EXAMPLE 1

A mixture of 25.2 parts of diketene, 62.7 parts of bromotrichloromethane and 1.5 parts of azobisisobutyronitrile dissolved in 978 parts of carbon tetrachloride was irradiated by UV light at room temperature (20°–25° C.) for 5 hours. The mixture was evaporated at the water pump and the product, 4-bromo-4-(2,2,2-trichloroethyl)-oxetan-2-one, was obtained as a yellow oil which crystallised on cooling. Recrystallisation of this material three times from light petroleum ether (b.p. 40°–60° C.) gave white needles m.p. 55°–56° C.

Calculated for $C_5H_4BrCl_3O_2$: C 21.27; H 1.43 Found: C 21.09; H 1.53.

EXAMPLE 2

2.0 parts of benzoyl peroxide (containing 25% of water) were dissolved in 163 parts of carbon tetrachloride and dried over magnesium sulphate. To the filtered dry solution were added 42 parts of diketene and the resulting solution was added dropwise over 5 hours to 815 parts of refluxing carbon tetrachloride. After completion of the addition the mixture was heated for a further 1 hour, then evaporated to dryness on the water pump. Extraction of the product into hot petroleum ether gave 4-chloro-4-(2,2,2-trichloroethyl)oxetan-2-one, shown to be 95% pure by GLC (gas liquid chromatography).

Distillation of a portion of the extracted material gave an analytically pure sample, b.p. 70°–75° C. at 0.013 mb(millibar).

Calculated for $C_5H_4Cl_4O_2$ C 25.25; H 1.69; Cl 59.61 Found: C 25.47; H 1.87; Cl 59.62.

EXAMPLE 3

210 parts of freshly distilled diketene and 30 parts of bis-(t-butylcyclohexyl)perdicarbonate were dissolved in 795 parts of carbon tetrachloride. This solution was added dropwise over 1 hour, with stirring, to 3180 parts of carbon tetrachloride held at reflux temperature in an atmosphere of dry nitrogen. When the addition was complete, stirring at reflux temperature was continued for 1 hour and the solution was then allowed to cool. The excess carbon tetrachloride was distilled off on a rotary evaporator under water pump vacuum at a bath temperature of 30°–40° C. The crude product was purified by distillation on a wiped-wall still giving pure 4-chloro-4-(2,2,2-trichloroethyl)oxetan-2-one.

EXAMPLE 4

A carbon tetrachloride solution containing 26.35 parts diketene and 3.76 parts of bis-(t-butylcyclohexyl)-perdicarbonate per 1592 parts of carbon tetrachloride was pumped through a two vessel cascade at such a rate as to give residence time of 60 minutes (residence time=vessel volume/volume pumped per minute). The vessels were stirred vigorously and heated at carbon tetrachloride reflux temperature. The product stream contained a little unreacted diketene, 4-chloro-4-(2,2,2-trichloroethyl)oxetan-2-one and carbon tetrachloride.

EXAMPLE 5

A mixture of 8.4 parts of diketene, 33.1 parts of carbon tetrabromide, 0.5 parts of bis-(t-butylcyclohexyl)-perdicarbonate and 326 parts of carbon tetrachloride was heated at 60° C. for 2 hours, then evaporated at the water pump. The residue was recrystallised twice from light petroleum ether (b.p. 40°–60° C.) and the product, 4-bromo-4-(2,2,2-tribromoethyl)oxetan-2-one, obtained as white needles, m.p. 71°–73° C.

Calculated for $C_5H_4Br_4O_2$ C 14.45; H 0.97; Br 76.89; Found: C 14.75; H 0.97; Br 76.20.

EXAMPLE 6

A mixture of 8.4 parts of diketene, 19.2 parts of ethyl trichloroacetate and 1.3 parts of bis-(t-butylcyclohexyl)-perdicarbonate was added dropwise over 3 hours to 96 parts of ethyl trichloroacetate stirred at 85° C. in a nitrogen atmosphere. After the addition, the mixture was stirred at 85° C. for a further ½ hour, then the unreacted starting materials were removed on a wiped wall still at 90° C./0.27 mb. The residue was distilled twice in a Kugelrohr at 100° C./0.33 mb. IR and NMR on the distillate showed the major component to be 4-chloro-4-(2,2-dichloro-2-ethoxycarbonyl-ethyl)oxetan-2-one.

EXAMPLE 7

1.68 parts of diketene and 0.4 parts of bis-(t-butylcyclohexyl)perdicarbonate were dissolved in 25 parts n-hexane and added over 1 hour to a stirred solution of 5.53 parts of 1-chloro-1,1-dibromotrifluoroethane in 25 parts n-hexane at 60° C. The mixture was stirred a further 1.5 hours at 60° C., then cooled to room temperature. The solution was decanted from an insoluble oil, then evaporated cold in vacuo to give 4-bromo-4-(2-chloro-2-bromo-3,3,3-trifluoropropyl)oxetan-2-one as a mobile yellow oil, with a characteristic I.R. carbonyl frequency of 1860 cm$^{-1}$.

EXAMPLE 8

A mixed culture of slime-forming bacteria including *Pseudomonas aeruginosa, Enterobacter aerogenes, Escherichia coli, Proteus vulgaris, Bacillus mycoides* and *Staphylococcus aureus* in saline containing $10^7$ organisms/ml was treated with 30 ppm of the product of Example 2. After one hour, the number of organisms had been reduced to $10^2$ organisms/ml and within 24 hours all the bacteria had been killed, thereby demonstrating the high bacteriocidal activity of the product of Example 2.

EXAMPLE 9

Test demonstrating algistatic activity

The organisms against which the compounds are to be tested are grown in an Erlenmeyer flask in a nutrient medium under sterile conditions on a shaking water bath at 18° C. with exposure (14 hours in light alternating with 10 hours in the dark).

Tests are carried out against three algae, namely the blue algae
(a) Phormidium foveolarum (A) which lives in polluted water or moist earth and forms trichomes;
the green algae
(b) the simple filament-forming Ulothrix subtilissima (B) generally found at colder times of the year in rapidly flowing water;
and the algae with brown chromatophors
(c) the widespread, unbranched filament-forming Tribonema aequale (C) occurring in bodies of water especially in the spring at low temperature or in the autumn, even in mild winters.

The composition of the medium is as follows (according to Algae broth, Difco Laboratories):
1.0 g of NaNO$_3$,
0.05 g of NH$_4$Cl,
0.058 g of CaCl$_2$,
0.5 g of MgSO$_4$.7 H$_2$O,
0.25 g of K$_2$HPO$_4$,
0.003 g of FeCl$_3$,
dissolved in 1 liter of distilled water. The nutrient medium treated with the biocide is innoculated with the respective algae suspension such that a final dilution of 1/100 (algae divided with a stirrer) is attained. Evaluation is made after a 3 week incubation in the Erlenmeyer flask on a shaking water bath. The activity is reported as the minimum inhibitory concentration (MIC in mg/l) which indicates that algicide concentration at which the growth of the algae is still inhibited. The results are summarised in Table 1.

TABLE 1

| Compound of formula | Minimum inhibitory Concentration, MIC mg/l | | |
|---|---|---|---|
| | Phormidium foveolarum | Ulothrix subtilissima | Tribonema aequale |
| Product of Example 2 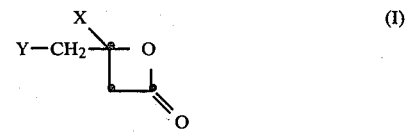 | 30 | 30 | 30 |

What we claim is:
1. A compound having the formula I

$$Y-CH_2 \overset{X}{\underset{}{\diagdown}} \begin{array}{c} O \\ \diagdown \diagup \\ O \end{array} \quad (I)$$

wherein X is a chlorine, bromine or iodine atom and Y is a residue having the formula R$^1$R$^2$R$^3$C-, wherein R$^1$ and R$^2$ are the same or different and each is a fluorine, chlorine or bromine atom and R$^3$ is a hydrogen, fluorine, chlorine or bromine atom, a group -CR$^4$R$^5$R$^6$, a cyano group, a group -COR$^7$ or -PO(R$^8$)$_2$ wherein R$^4$, R$^5$, R$^6$, independently, are F, Cl or Br, R$^7$ and R$^8$ are the same or different and each is a chlorine atom or a group -OR$^9$ wherein R$^9$ is a C$_1$-C$_4$ straight chain or branched alkyl group with the proviso that when X is a chlorine atom, none of R$^1$, R$^2$, R$^3$, R$^4$, R$^5$ and R$^6$ can be a bromine atom.

2. A compound as claimed in claim 1 wherein X is a chlorine or bromine atom.

3. A compound as claimed in claim 1 wherein R$^1$, R$^2$ and R$^3$ are each a fluorine, chlorine or bromine atom.

4. A compound as claimed in claim 1 which is selected from the group consisting of 4-chloro-4-(2,2,2-trichloroethyl)oxetan-2-one, 4-bromo-4-(2,2,2-trichloroethyl)oxetan-2-one, 4-bromo-4-(2,2,2-tribromoethyl)oxetan-2-one, 4-chloro-4-(2,2-dichloro-2-ethoxycarbonylethyl)oxetan-2-one, and 4-bromo-4-(2-chloro-2-bromo-3,3,3-trifluoropropyl)oxetan-2-one.

5. A process of producing a compound of formula I as claimed in claim 1, comprising reacting diketene with a compound XY wherein X and Y are as defined in claim 1, in the presence of an agent capable of forming free radicals.

6. A process as claimed in claim 5 wherein the compound XY is a tetrahalomethane or a trihalomethyl compound.

7. A process as claimed in claim 5 wherein the compound XY is carbontetrachloride, carbontetrabromide, bromotrichloromethane, ethyltrichloroacetate, trichloromethylphosphonyl dichloride, trichloroacetonitrile, 1-chloro-1,1-dibromotrifluoroethane or hexachloroethane.

8. A process as claimed in claim 5 wherein the agent capable of forming free radicals is an organic peroxide; an organic azo compound; or a combination of an organic peroxide or an organic azo compound with ultraviolet radiation.

9. A process as claimed in claim 5 which is carried out in a continuous manner.

* * * * *